United States Patent [19]

Callaghan et al.

[11] Patent Number: 5,477,851
[45] Date of Patent: Dec. 26, 1995

[54] LARYNGEAL MASK ASSEMBLY AND METHOD FOR REMOVING SAME

[76] Inventors: Eric B. Callaghan; Mark L. Callaghan, 17 Lake View Dr., Marquette, Mich. 49855

[21] Appl. No.: 378,775

[22] Filed: Jan. 26, 1995

[51] Int. Cl.$^6$ .......................... A61M 16/00; A61M 29/00
[52] U.S. Cl. ................ 128/207.15; 128/200.23; 604/96
[58] Field of Search .................. 128/200.23, 207.14, 128/207.15, 200.24, 4, 10; 604/96, 97, 98, 99, 100, 101, 102, 103

[56] References Cited

U.S. PATENT DOCUMENTS

| | | | |
|---|---|---|---|
| 4,509,514 | 4/1985 | Brain | 128/207.15 |
| 4,685,457 | 8/1987 | Donenfeld | 128/207.14 |
| 4,988,356 | 1/1991 | Crittenden et al. | 606/192 |
| 4,995,388 | 2/1991 | Brain | 128/207.15 |
| 5,019,042 | 5/1991 | Sahota | 604/101 |
| 5,033,466 | 7/1991 | Weymuller, Jr. | 128/207.15 |
| 5,174,283 | 12/1992 | Parker | 128/200.26 |
| 5,205,822 | 4/1993 | Johnson et al. | 604/96 |
| 5,241,956 | 9/1993 | Brain | 128/207.15 |
| 5,249,571 | 10/1993 | Brain | 128/207.14 |
| 5,277,178 | 1/1994 | Dingley | 128/200.26 |
| 5,282,464 | 2/1994 | Brain | 128/207.15 |
| 5,285,778 | 2/1994 | Mackin | 128/207.15 |
| 5,287,848 | 2/1994 | Cubb | 128/200.26 |
| 5,297,547 | 3/1994 | Brain | 128/207.15 |
| 5,303,697 | 4/1994 | Brain | 128/207.15 |
| 5,383,853 | 1/1995 | Jung et al. | 604/96 |
| 5,389,087 | 2/1995 | Miraki | 604/247 |

FOREIGN PATENT DOCUMENTS

| | | |
|---|---|---|
| 2366844 | 2/1992 | France . |
| 2308400 | 6/1992 | Germany . |
| 685295 | 11/1991 | U.S.S.R. . |

Primary Examiner—Edgar S. Burr
Assistant Examiner—Eric P. Raciti
Attorney, Agent, or Firm—Reising, Ethington, Barnard & Perry

[57] ABSTRACT

A laryngeal mask assembly (10) includes an artificial airway tube (14) and an inflatable mask (26). The mask (26) is forced into the mouth (20) of a patient (12) to an operating position adjacent the larynx (21). A scoping instrument (22) is sent through the artificial airway tube (14) and the inflatable mask (26) to locate the vocal cords (23) and trachea (35). The artificial airway tube (14) and inflatable mask (26) are removed, keeping the scoping instrument (22) in a position within the trachea (35) whereafter the laryngeal mask assembly (10) is removed by peeling it off the scoping instrument (22) using the slit (34) creating by the overlapping edges (36, 38).

7 Claims, 2 Drawing Sheets

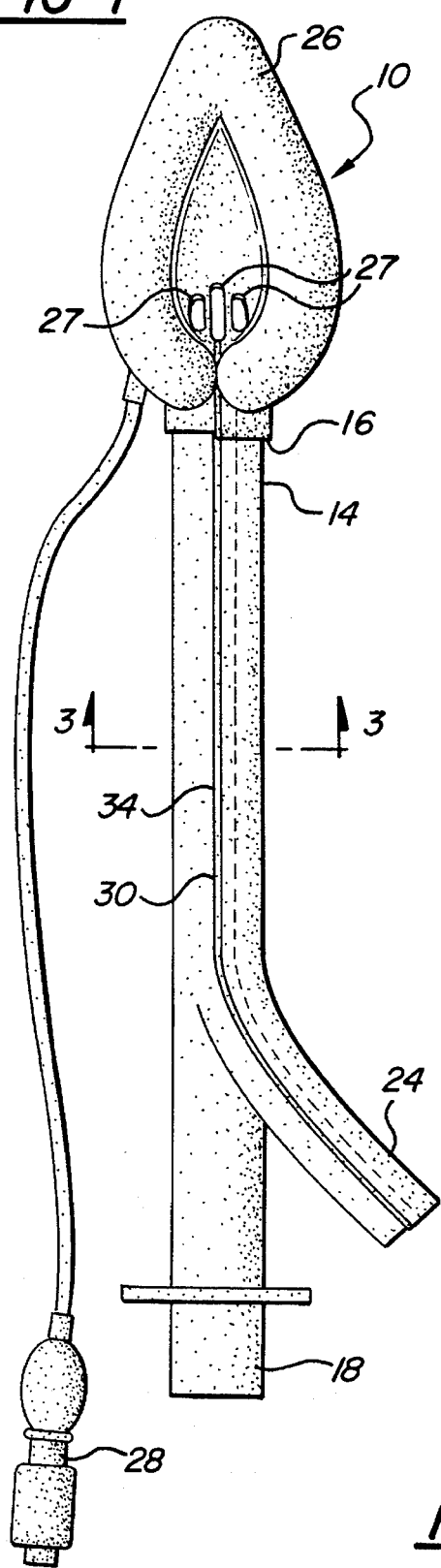
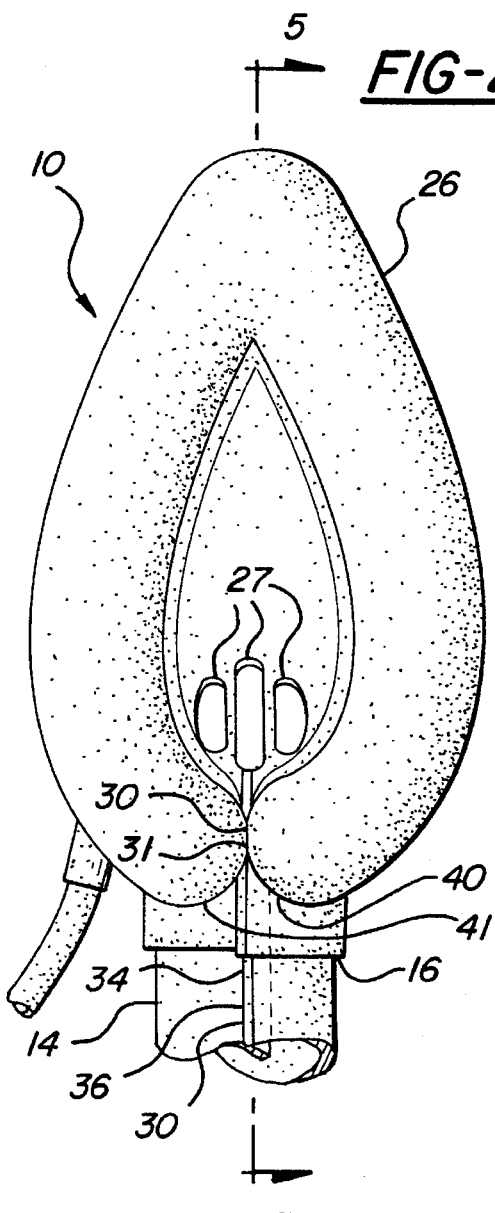
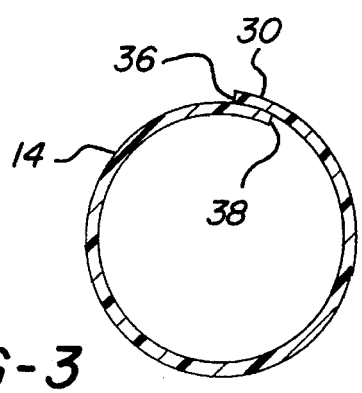

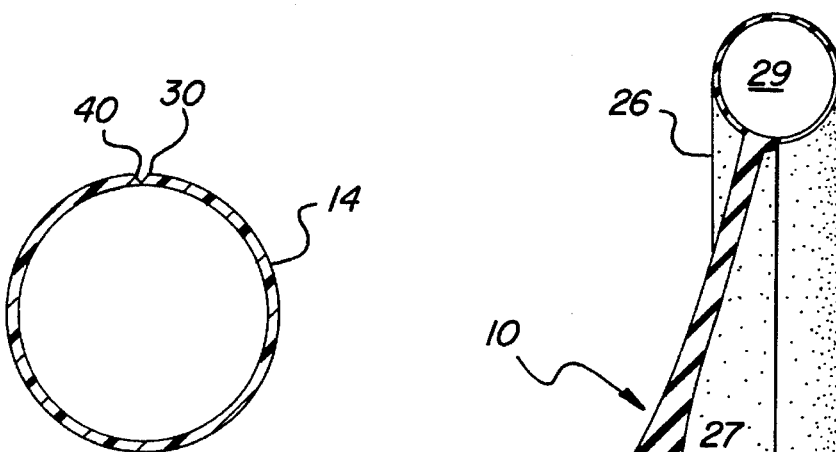
FIG-4
FIG-5
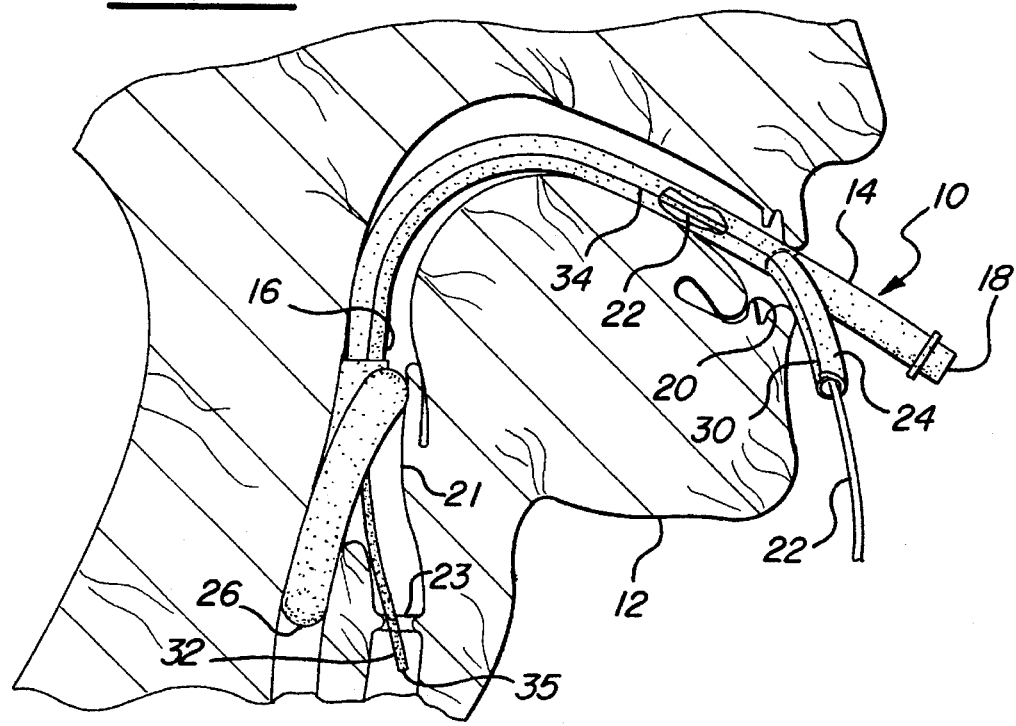
FIG-6

5,477,851

LARYNGEAL MASK ASSEMBLY AND METHOD FOR REMOVING SAME

TECHNICAL FIELD

The invention related to artificial airway assemblies. More particularly, the invention relates to artificial airway assemblies which are easily removable after locating the vocal cord of a patient.

DESCRIPTION OF RELATED ART

In recent years, several improvements have been made in the artificial airway technology. U.S. Pat. No. 4,509,514, issued to Brain on Apr. 9, 1985, discloses an artificial airway assembly used to facilitate lung ventilation in an unconscious patient. The laryngeal mask provides a seal around the larynx. A tube connected to the laryngeal mask allows air to pass therethrough and through the mask to facilitate breathing. A pump is used to inflate and deflate the laryngeal mask to facilitate the inserting and removing of the laryngeal airway in the patients mouth, as well as to improve the seal around the larynx. Although this artificial airway assembly provides an unblocked airway for an unconscious patient to facilitate the breathing of the patient, the system does not secure the airway in such a manner as an endotracheal tube which resides in the trachea and prevents aspiration of gastric contents in a more definitive manner.

SUMMARY OF THE INVENTION AND ADVANTAGES

The assembly is an artificial airway assembly for ventilating a patient as well aiding in the tracheal intubation of patients in which traditional procedures would be difficult. The artificial airway assembly comprises a flexible airway tube having a patient insertion end and a breathing tube receiving end. The flexible airway tube allows a scoping instrument to pass therethrough to an operating position to view the vocal cords and trachea of the patient. A mask is fixedly secured to the patient insertion end of the flexible airway tube wherein the mask is capable of conforming to the space immediately adjacent the larynx of the patient to properly position the scope instrument. The artificial airway assembly is characterized by removing means for removing the flexible airway tube from the scope instrument while maintaining the scoping instrument in the operating position.

The advantages associated with the subject invention includes the ability to remove the laryngeal mask from the patient's airway while maintaining the end of the scoping instrument in position in the trachea allowing an endotracheal tube to be guided over the scoping instrument, thereby securing the airway in a definitive manner and allowing for ventilation through the endotracheal tube and prevention of aspiration of gastric contents.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a top view of the preferred embodiment of the subject invention;

FIG. 2 is a top view partially cut away of the mask of the preferred embodiment of the subject invention;

FIG. 3 is a cross-sectional view taken along lines 3—3 of FIG. 1;

FIG. 4 is a cross-sectional view of an alternative embodiment of the artificial airway tube;

FIG. 5 is a cross-sectional view taken along lines 5—5 of FIG. 2; and

FIG. 6 is a side view partially cut away of a patient with the preferred embodiment of the subject invention inserted in the operating position.

DETAILED DESCRIPTION OF THE DRAWINGS

Turning to the enclosed sketches, an artificial airway assembly is generally shown at 10. The artificial airway 10 ventilates a patient 12 while when the patient 12 can not breath on her own or needs some form of respiratory assistance. Typically, this occurs when the patient 12 is unconscious during surgery. The artificial airway assembly 10 comprises a flexible airway tube 14. The flexible airway tube 14 includes a patient insertion end 16 and a breathing tool receiving end 18. The patient insertion end 16 is inserted into the patient's mouth 20 and extended into a position adjacent the larynx 21. The breathing tool receiving end 18 is attached to a breathing tool (not shown) such as a ventilating bag or a ventilating machine.

The flexible airway tube 14 allows a scoping instrument 22 to pass therethrough to an operating position to view the vocal cords 23 and trachea 35 of the patient 12. In the preferred embodiment, the scoping instrument 22 is fiber optic scope which extends along the length of the flexible airway to a tube 14 and out the patient insertion end 16 to view the vocal cords 23 and enter the trachea 35. The flexible airway tube 14 includes a second branch 24 which is in fluid communication with the flexible airway tube 14. The second branch 24 guides the scoping instrument 22 into the flexible airway tube 14 and allows for uninterrupted ventilation to continue through the breathing tool receiving end 18. The scoping instrument 22, i.e., the fiber optic scope, is not part of the subject invention wherein any type of scoping instrument may be used to determine the location of the patient insertion end 16.

A mask 26 is fixedly secured to the patient insertion end 16 of the flexible airway tube 14. The mask includes holes 27 allowing air and the scoping instrument 22 to pass therethrough. The mask 26 is capable of conforming to the space immediately adjacent the larynx 21 of the patient 12 to properly position the scoping instrument 22. More specifically, the mask 26 is made of a resilient rubber-like material having a hollow space 29 capable of being inflated and deflated to accommodate for the space adjacent the larynx 21. Because the mask 26 is resiliently deformable, the natural configuration of the mask 26 is in the deflated position. A valve assembly 28 allows air to pass in and out of the mask 26 which allows for easier insertion when the mask 26 is deflated and a better seal around the larynx 21 when the mask 26 is inflated. Typically, air is injected or withdrawn from the mask 26 with a syringe. The inflatable portion of the mask 26 has ends 40, 41 which come together and abut upon inflation of the mask 26 to provide a seal. In the deflated position, the ends 40, 41 move away from each other to facilitate removal of the device 10 and the scoping instrument 22.

The subject invention is characterized by removing means 30 for removing the flexible airway tube 14 and the mask 26 from the scoping instrument 22 while maintaining the scoping instrument 22 in the operating position as shown in FIG. 6. Once the scoping instrument 22 is in place, artificial airway assembly 10 is removed, a smaller flexible airway tube (not shown) can be manipulated to pass over the fiber optic scope into the same position as the end 32 of the scoping instrument 22. Therefore, once the smaller airway tube is inserted into the same position as the scoping instrument end 32, the scoping instrument is removed and the airway is secure.

The removing means 30 includes a slit 34 extending along the flexible airway tube 14 and a position 31 of the mask 26. The slit 34 allows the artificial airway assembly 10 to be removed from the scoping instrument 22 while the scoping instrument 22 remains operational in the operating position. The slit 34 creates two opposing side edges 36, 38. The opposing side edges 36, 38 over lap each other such that the artificial airway assembly 10 is substantially sealed between the patient insertion end 16 and the breathing tool receiving end 18.

As may be seen in FIG. 4, the removing means 30 may comprise a scored portion 40 which is weakened at that point allowing the assembly 10 to be torn away when pressure is applied to the assembly 10 to pull the assembly 10 away from the scope instrument 22.

In operation, the method for intubating a patient 12 using an artificial airway assembly 10 which includes a mask 26 and a flexible airway tube 14 and a scoping device 22 comprises the steps of: inserting the artificial airway assembly 10 into the mouth 20 of the patient while positioning the mask 26 adjacent the larynx 21; moving the scoping device 22 through the artificial airway assembly 10 and the mask 26 into the trachea 35; removing the artificial airway assembly 10 from the mouth 20 of the patient 12; and peeling the artificial airway assembly 10 off the scoping device 22. The peeling of the artificial airway assembly 10 off the scoping device 22 occurs when the scoping device is maintained in the operating position and while the scoping device 22 is operating.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

We claim:

1. An artificial airway assembly (10) for ventilating a patient (12) and utilizing a scoping device in the airway of a patient, said artificial airway assembly (10) comprising:

a flexible airway tube (14) having a patient insertion end (16) and a breathing tool receiving end (18), said flexible airway tube having pass through means for allowing a scoping instrument (22) to pass therethrough to an operating position to view vocal cords and trachea of the patient (12);

a mask (26) fixedly secured to said patient insertion end (16) of said flexible airway tube (14), said mask (26) having conforming means for conforming to a space immediately adjacent the larynx of the patient (12) to properly position the scoping instrument (22), said artificial airway assembly (10) characterized by removing means (3) for removing said flexible airway tube (14) and mask (26) from the scoping instrument (22) while maintaining the scoping instrument (22) in the operating position.

2. An assembly (10) as set forth in claim 1 further characterized by said removing means (30) including a slit (34) extending along said flexible airway tube (14).

3. An assembly (10) as set forth in claim 2 further characterized by said slit (34) extending through a portion of said mask (26).

4. An assembly (10) as set forth in claim 3 further characterized by said slit (34) creating two opposing side edges (36, 38).

5. An assembly (10) as set forth in claim 4 further characterized by said two opposing side edges (36, 38) overlapping each other such that said artificial airway assembly (10) is substantially sealed between said patient insertion end (16) and said breathing tool receiving end (18).

6. An assembly (10) as set forth in claim 5 further characterized by said flexible airway tube (14) including a second branch (24) in fluid communication with said flexible airway tube (14) for guiding the scoping instrument (22) into flexible airway tube (14).

7. A method for intubating a patient (12) using an artificial airway assembly (10) including a mask (26) and flexible airway tube (14), and a scoping device (22), the method comprising the steps of:

inserting the artificial airway assembly (10) into the mouth (20) of a patient (12);

positioning the mask (26) adjacent the larynx;

moving the scoping device (22) through the artificial airway assembly (10) and the mask (26);

removing the artificial airway assembly (10) from the mouth (20) of the patient (12); and peeling the artificial airway assembly (10) off the scoping device (22).

\* \* \* \* \*